United States Patent [19]

Osberghaus

[11] 4,032,629

[45] June 28, 1977

[54] SKIN TREATING AGENT CONTAINING POLYALDEHYDOPOLYCARBOXYLATE POLYMERS AND PROCESS

[75] Inventor: Rainer Osberghaus, Dusseldorf-Urdenbach, Germany

[73] Assignee: Henkel & Cie G.m.b.H., Dusseldorf-Holthausen, Germany

[22] Filed: Jan. 28, 1975

[21] Appl. No.: 544,810

[30] Foreign Application Priority Data

Apr. 20, 1974 Germany ......................... 2419046

[52] U.S. Cl. ................................... 424/78; 424/59; 424/60; 424/73; 424/81; 424/170; 424/357; 424/365
[51] Int. Cl.$^2$ ................. A61K 31/74; A61K 31/78
[58] Field of Search ............................... 424/81, 78

[56] References Cited

UNITED STATES PATENTS

| | | | |
|---|---|---|---|
| 3,141,864 | 7/1964 | Rink | 424/78 X |
| 3,142,661 | 7/1964 | Brendlein et al. | 424/78 X |
| 3,405,095 | 10/1968 | Hartel et al. | 424/78 X |
| 3,825,498 | 7/1974 | Altenschopfer | 424/78 X |

*Primary Examiner*—Dale R. Ore
*Attorney, Agent, or Firm*—Hammond & Littell

[57] ABSTRACT

The present invention relates to compositions for the treatment of the skin containing up to 25% by weight of at least one polymer having carboxyl or carboxylate groups and aldehyde groups of chiefly rectilinear or cross-linked C—C compounds, the ratio of carboxyl or carboxylate groups to aldehyde groups in said polymer being in excess of 0.5:1, and particularly between 1.1:1 and 16:1, preferably between 2:1 and 9:1, and the polymerization degree being at least 3, preferably 3 to 100; as well as the method of skin treatment.

10 Claims, 2 Drawing Figures

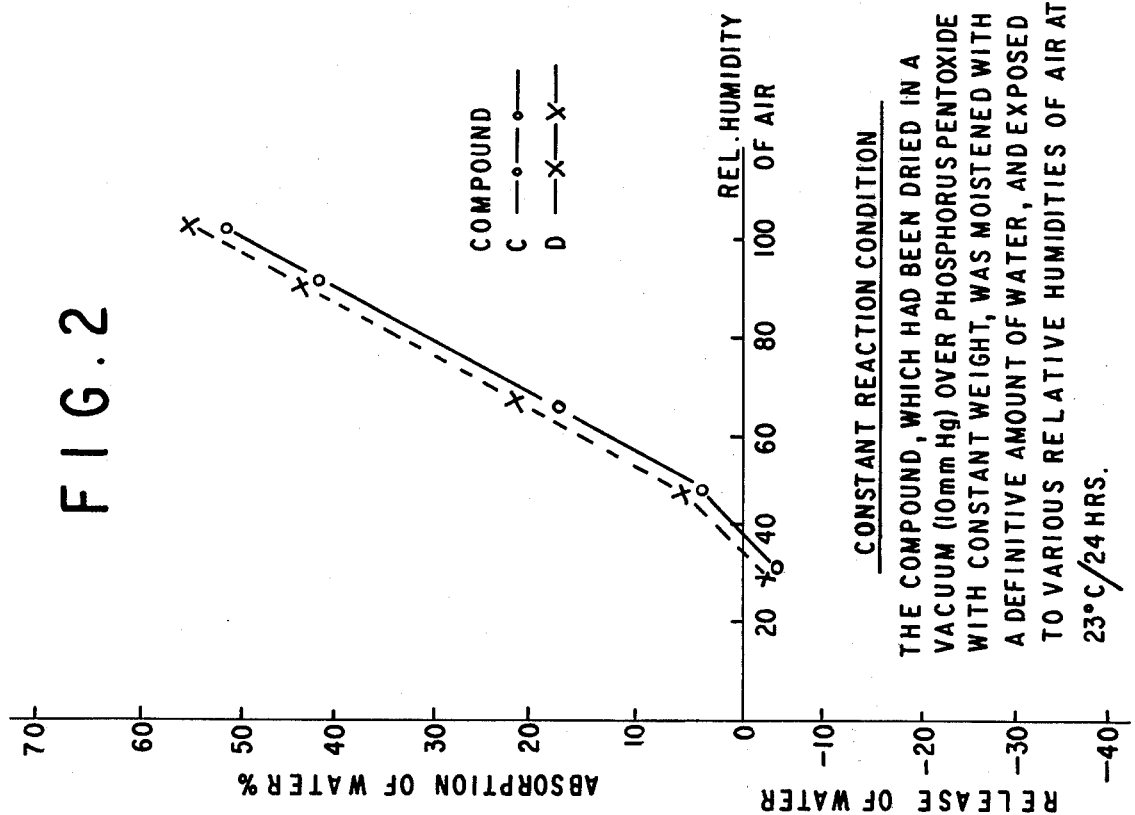
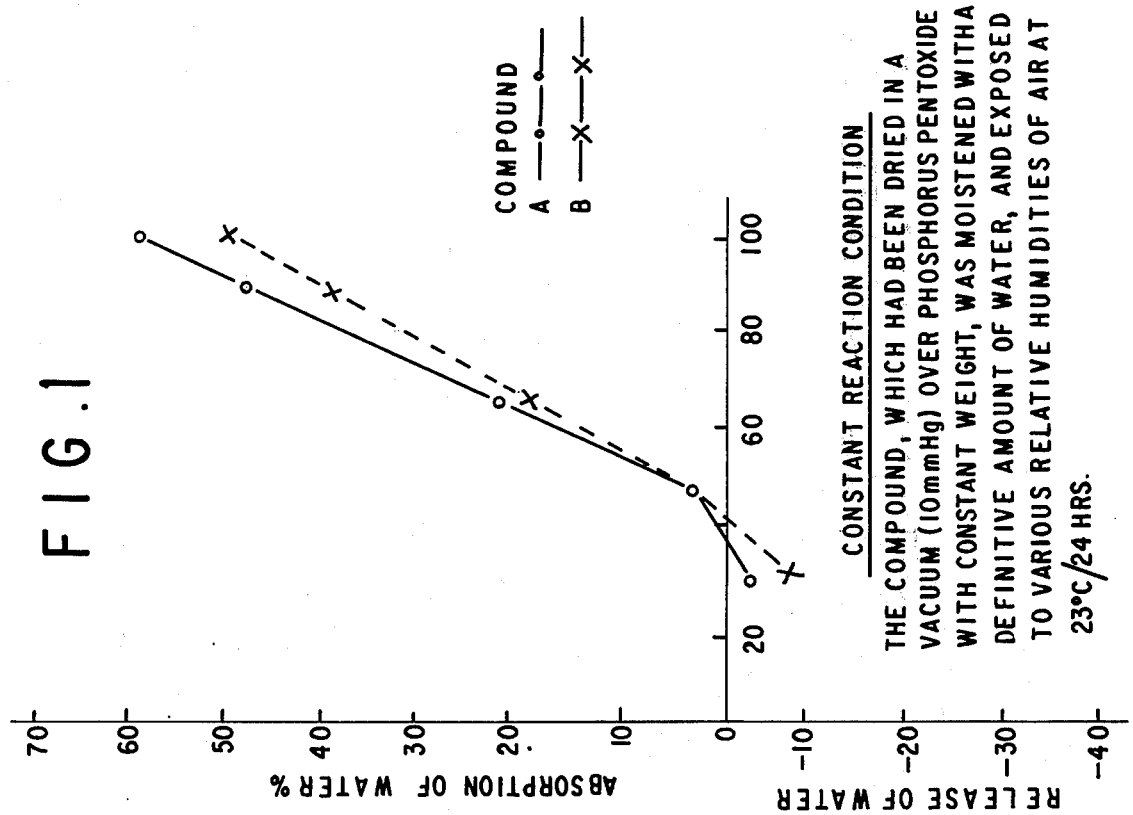

SKIN TREATING AGENT CONTAINING POLYALDEHYDOPOLYCARBOXYLATE POLYMERS AND PROCESS

It is generally known that protective measures for healthy skin include, among other things, that the skin surface maintains a certain hygroscopicity. If the substances, on which this hygroscopicity and its constant restoration depend, are removed from the skin by environmental influences, such as repeated washing with substances which have a strong wetting and extracting effect, and the influences of chemicals or severe weather, alterations are produced in the horny layer which can greatly reduce the protective action of the skin against harmful environmental influences.

The object of the present invention is to provide a skin care or skin protection agent, by means of which the functional capacity of the skin may be maintained or increased in spite of harmful environmental influences, and which effectively support the restoration of the horny layer, should any damage have been incurred.

Another object of the present invention is the development of a cosmetic composition for the care and protection of the skin of warm-blooded animals consisting essentially of from 1 to 20% by weight of at least one polyaldehydopolycarboxyl polymer having a polymer chain containing substantially units selected from the group consisting of

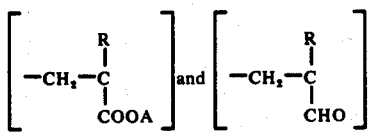

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyaldehydopolycarboxyl polymer having a ratio of —COOA groups to C=O groups of from 0.5:1 to 16:1 and a degree of polymerization of from 3 to 100, and the remainder inert cosmetic excipients.

A further object of the invention is the development of a process for the care and protection of the skin of warm-blooded animals comprising topically applying to the skin a safe but effective amount of the above composition.

These and other objects of the present invention will become more apparent as the description thereof proceeds.

FIGS. 1 and 2 are curves of the equilibrium dampness of various polyaldehydopolycarboxyl polymers according to the invention.

The above objects have been achieved by the discovery of a skin care or skin protective agent comprising conventional constitutents such as emulsifiers, fatty substances, plant extracts, solvents, scents, thickeners and preservatives, and from 1 to 20% by weight, preferably 3 to 10% by weight, based on the weight of the whole agent of at least one polyaldehydopolycarboxyl polymer having a polymer chain containing carboxyl or carboxylate groups and aldehyde groups and chiefly containing rectilinear or cross-linked C—C compounds, and the minimum degree of polymerization being 3, with a range of preferably 3 to 100. Preferably, the ratio of carboxyl or carboxylate groups to aldehyde groups in said polymers should exceed 0.5:1, particularly being between 1.1:1 and 16:1, preferably between 2:1 and 9:1.

The polymers to be used in accordance with the invention are predominantly built up from units of the general formulae

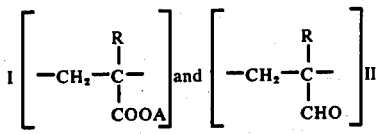

wherein A represents hydrogen, a valence of a mono- or polyvalent metal particularly an alkali metal, preferably sodium or an ammonium or amine or alkanolamine, and R represents an alkyl group having 1 to 6 carbon atoms, in particular a methyl group, or preferably a hydrogen atom, wherein the units I and II can be disposed in any sequence desired, and the average frequency of these units corresponds to a ratio of carboxyl or carboxylate groups to aldehyde groups, which exceeds 0.5:1 and is particularly between 1.1:1 and 16:1, and preferably between 2:1 and 9:1, and their degree of polymerization is from 3 to 100.

These polymer generally have the following formula, where R is H, without being bound to the sequence of the units of the formula

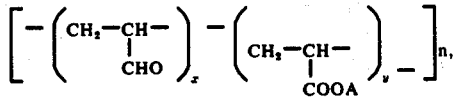

wherein A has the above-indicated meanings, wherein the units containing the aldehyde and carboxylate groups can be arranged in any sequence desired and their degree of polymerization is 3 to 100.

In the formula $x$ represents basic/molar percentages CHO/100*

$y$ represents basic/molar percentages COO/100*

*Basic molar percentage according to Trommsdorff(Inaugural diss. Freiburg i. Br. 1931 ).

More particularly, the present invention relates to a cosmetic composition for the care and protection of the skin of warm-blooded animals consisting essentially of from 1 to 20% by weight of at least one polyaldehydopolycarboxyl polymer having a polymer chain containing substantially units selected from the group consisting of

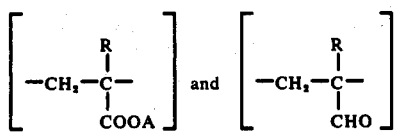

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyaldehydopolycarboxyl polymer having a ratio of —COOA groups to C=O groups of from 0.5:1 to 16:1 and a degree of polymerization of from 3 to 100, and the remainder inert cosmetic excipients; as well as a process for the care and protection of the skin of warm-blooded animals comprising topically applying to the skin a safe but effective amount of the above composition.

The polymers to be used in accordance with the invention are extremely suitable for maintaining or restoring the water retention of the skin and thus for keeping the skin soft, supple and fully capable of performing its function.

The production of these polyaldehydopolycarboxyl polymers is preferably effected by the oxidative homopolymerization of acrolein or by the oxidative copolymerization of acrolein and acrylic acid or alkenoic acids having 3 to 8 carbon atoms, as described in the German Published Application DOS 1,904,940.

Peroxides or peracids, but preferably hydrogen peroxide, are used as oxidation agents. The carboxyl group content in the polymer can, on the one hand, be influenced by the ratio of the oxidation agent amount to the acrolein amount, and on the other hand by the utilization of acrylic acid as comonomer. The greater the ratio of the oxidation agent amount to the acrolein amount, the greater the number of carboxyl groups present in the polymer, and vice versa. Since the peroxy compound simultaneously acts as a regulator, the degree of polymerization is influenced by the amount of this compound which is used, and the polymerization degree decreases as the amount of oxidation agent increases. On the other hand, the degree of polymerization can be influenced by the utilization of acrylic acid as comonomer and increases as the content of acrylic acid in the comonomer mixture rises.

The homopolymerization of acrolein or the copolymerization of acrolein and acrylic acid can be carried out independently of the desired carboxyl group content in the polymer, either by solution polymerization or precipitation polymerization, preferably in an aqueous medium. The polyaldehydopolycarboxylic acids which are obtained in this manner and which are of the above-mentioned formula, without being bound to the sequence of the units of the formula, are neutralized with the appropriate basic compound, so that the neutral solutions of the salts of the polyaldehydopolycarboxylic acids are obtained, from which said salts of polyaldehydopolycarboxylic acids can easily be isolated by evaporation of the water. Care must be taken, however, not to exceed the neutral pH of 7 in the neutralization step.

The polymers to be used in accordance with the invention are odorless, completely stable, colorless to pale yellow, possess excellent physiological compatibility and have no disadvantageous effects on the skin care and skin protection agents in which they are mixed.

It is known that in addition to other factors a certain hygroscopicity is necessary for the protection of a healthy skin. If the skin is deprived of the substances which are responsible for this hygroscopicity as well as its continual restoration by environmental circumstances such as repeated washings, effect of chemicals or strong weather influences, alterations occur in the stratum corneum, as a result of which the protective effect of the skin against harmful influences of the environment may be considerably diminished.

It was found that the functional capacity of the skin may be maintained or restored even to a higher degree than before if it is treated with agents for the care and protection of the skin, which besides the customary constituents include from 1 to 20% by weight, preferably 3 to 10% by weight, based on the total composition of the polyaldehydopolycarboxyl polymers in accordance with the invention.

Among the compositions for the care and protection of the skin having special skin-caring properties due to the addition of the polyaldehydopolycarboxyl polymers in accordance with the invention are emulsions of oil-in-water or water-in-oil type. These are the conventional day creams, baby creams, night creams and nourishing creams, cleansing creams, skin protection creams, glycerol creams, creams with special additives of animal or vegetable origin, sun protection or sun tanning creams, and sun protection emulsions, face lotions and after-shave lotions. The incorporation of the agents for care and protection of the skin may take place in the known manner by simple stirring-in or dissolving. In addition to the polyaldehydopolycarboxyl polymers in accordance with the invention, the cosmetic preparations may contain the constituents normally present in them such as emulsifiers, fatty substances, plant extracts, preservatives, perfumes, solvents, thickeners and preservatives in the customary amounts. The pH value of the agents for the care and protection of the skin may be in the acid to neutral region (pH 5 – 7.0 ) and is approximately adjusted to weakly acid values of about pH 6.

The following examples are intended to illustrate the subject of the invention without, however, limiting it to these examples.

EXAMPLES

Several polymers having carboxyl or carboxylate and aldehyde groups are to be mentioned first of all, which can be used as skin moisturizing agents in the skin care and skin protection agents according to the invention.

Product A Poly-(aldehydocarboxylic acid)-sodium salt, oxidative copolymer of acrolein and acrylic acid, neutralized with NaOH solution, median polymerization degree of approximately 10.

430 ml of a mixture of 92% water, 7% acrylic acid and 1% acrolein was placed together with 400 ml of 30% hydrogen peroxide solution in a reactor. During stirring and heating from 55° C to 60° C, 365 ml of freshly distilled acrolein was added to the reaction mixture dropwise within approximately 5 hours. When all the acrolein had been added, the mixture was briefly heated to about 80° C. Thereafter, the mixture was cooled, reduced to approximately half its volume under vacuum and was neutralized to a pH of 6 with sodium hydroxide solution and brought to dryness under a vacuum. The polyaldehydocarboxylic acid from which the sodium salt was formed, had a COOH content of 80%, a C=O content of 20% and a median polymerization degree of 10.

The products which are shown hereinafter in Table I were produced in a corresponding manner.

TABLE I

| Product | Chemical Specification | Median polymerization degree | Carboxyl content (basic/molar %) * | Carbonyl content (basic/molar %) * |
|---|---|---|---|---|
| B | Polyaldehydocarboxylic acid-sodium salt; oxidative copolymerizate of 50 mol % acrolein and 50 mol % acrylic acid, neutralized with NaOH. | 50 | 90 | 10 |
| C | Polyaldehydrocarboxylic acid-triethanolamine salt; oxidative copolymerizate of 80 mol % of acrolein and 20 mol % of acrylic acid, neutralized with triethanolamine. | 15 | 77 | 13 |
| D | Polyaldehydrocarboxylic acid-sodium salt; oxidative acrolein polymerizate, neutralized with NaOH. | 5 | 80 | 6 |

* Functional groups per 100 monomer units in the molecule chain

The favorable action of the compounds, which are to be used in accordance with the invention, with regard to capacity for the absorption and retention of water, was also determined by means of test methods which are described more fully hereinafter. A process for determining the equilibrium dampness, which constitutes a gauge for the water retention capacity, is described in these tests.

1. Determination of the equilibrium dampness

The substances (about 300 to 500 mg) to be tested were moistened with a defined quantity of water and exposed for 24 hours at 23° C to various relative atmospheric humidities (1%, 30%, 47%, 65%, 89% and 100% relative humidity). The amount of water absorbed or desorbed was determined gravimetrically and plotted on a graph. The relative hunidity at which neither expulsion nor retention of water is effected, can be determined from the resultant curves (FIGS. 1 and 2). This value, which is designated as the equilibrium dampness, is a gauge for the water retention capacity of a substance. The lower the value, the more positive should be the assessment of the product. The steepness of the curve, in addition, indicated the water retaining capacity (hygroscopicity) of the substance.

These afore-mentioned measured value of the graphs (FIGS. 1 and 2 ) also confirm the suitability of the products which are to be used in accordance with the invention as skin moisture-containing agents in skin care and skin protection agents, since none of the products expel water until very low relative humidities have been reached. Even at low relative atmospheric humidities of $\geq$ 42%, the products A,B,C, and D absorb moisture from the surrounding atmosphere.

In the following, a few examples of cosmetic preparations containing substances in accordance with the invention as skin humectants, are given.

EXAMPLE 1

| Day cream, slightly greasy | Parts by weight |
|---|---|
| Fatty acid partial glyceride Cutina MD Dehydag | 6.0 |
| Stearic acid | 8.0 |
| Mixture of nonionic emulsifiers Emulgin C 700 Dehydag | 3.0 |
| 2-octyl-dodecanol | 4.0 |
| Vegetable oil | 3.0 |
| Paraffin oil | 5.0 |
| Triethanolamine | 0.4 |
| 1,2-propylene glycol | 3.0 |
| Product A | 3.0 |
| Nipagin M | 0.2 |

EXAMPLE 1-continued

| Day cream, slightly greasy | Parts by weight |
|---|---|
| Perfume oil | 1.0 |
| Water | 63.4 |

EXAMPLE 2

| Baby cream | Parts by Weight |
|---|---|
| Mixture of higher molecular esters, mainly mixed esters of pentaerythritol fatty acid ester and citric acid fatty alcohol ester Dehymuls E Dehydag | 7.0 |
| Decyl oleate | 10.0 |
| Vaseline | 10.0 |
| Wool fat | 5.0 |
| Boric acid | 0.2 |
| Talcum | 12.0 |
| Zinc oxide | 8.0 |
| Nipagin M | 0.2 |
| Product C | 5.0 |
| Water | 42.6 |

EXAMPLE 3

| Night cream | Parts by Weight |
|---|---|
| Colloidally dispersed mixture of 90 parts of cetyl-stearyl alcohol and 10 parts of sodium lauryl sulfate | 10.0 |
| 2-Octyl-dodecanol | 12.0 |
| Vegetable oil | 7.0 |
| Wool fat | 2.0 |
| Glycerol | 1.0 |
| Product B | 5.0 |
| Nipagin M | 0.2 |
| Perfume Oil | 1.0 |
| Water | 61.8 |

EXAMPLE 4

| Boro-glycerol cream | Parts by Weight |
|---|---|
| Colloidally dispersed mixture of 90 parts of cetyl-stearyl alcohol and 10 parts of sodium lauryl sulfate | 12.0 |
| 2-Octyl-dodecanol | 8.0 |
| Vegetable oil | 5.0 |
| Boric acid | 2.0 |
| Glycerol | 28.0 |
| Nipagin M | 0.2 |
| Product D | 3.0 |
| Water | 41.8 |

EXAMPLE 5

| Sun protection cream | Parts by Weight |
|---|---|
| Mixture of higher molecular esters with fatty substances Dehymuls K® Dehydag | 30.0 |
| Decyl oleate | 15.0 |
| Light protection agent | 5.0 |
| Nipagin M | 0.2 |
| Product A | 3.0 |
| Water | 46.8 |

EXAMPLE 6

| Face mask | Parts by Weight |
|---|---|
| Mixtures of fatty acid partial glyceride with emulsifiers Cutina LE Dehydag® | 12.0 |
| Decyl oleate | 4.0 |
| Vitamin oil | 5.0 |
| Kaolin | 2.0 |
| Rice starch | 3.0 |
| Nipagin M | 0.2 |
| Product B | 6.0 |
| Water | 67.8 |

EXAMPLE 7

| After-shave lotion | Parts by Weight |
|---|---|
| Oleyl/cetyl alcohol | 1.0 |
| Ethanol 96% | 40.0 |
| Menthol | 0.2 |
| Camphor | 0.2 |
| Peru balsam | 0.1 |
| Perfume | 0.5 |
| Sodium lactate | 3.0 |
| Boric acid | 0.5 |
| Product D | 7.0 |
| Water | 47.5 |

EXAMPLE 8

| Face lotion | Parts by Weight |
|---|---|
| Cucumber essence | 15.0 |
| Citric acid | 0.2 |
| Ethanol 96% | 15.0 |
| Product C | 10.0 |
| Perfume | 1.0 |
| Water | 58.8 |

In place of the compounds in accordance with the invention mentioned in the above examples, others of the products in accordance with the invention may be used with equally good success.

The preceding specific embodiments are illustrative of the practice of the invention. It is to be understood, however, that other expedients known to those skilled in the art, or given herein, may be employed without departing from the spirit of the invention or the scope of the appended claims.

I claim:

1. A cosmetic composition for maintaining a certain hygroscopicity for the protection of the skin of warm-blooded animals consisting essentially of an emulsion selected from the group consisting of oil-in-water and water-in-oil, having a pH between 5 and 7 and containing an emulsifier, water, from 1 to 20% by weight of at least one polyaldehydopolycarboxyl polymer having a polymer chain containing substantially units selected from the group consisting of

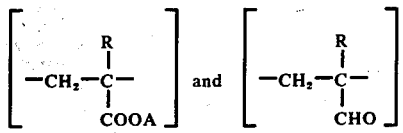

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyaldehydopolycarboxyl polymer having a ratio of —COOA groups to C=O groups of from 0.5:1 to 16:1 and a degree of polymerization of from 3 to 100, and the remainder inert cosmetic excipients.

2. The composition of claim 1 wherein said at least one polyaldehydopolycarboxyl polymer is present in an amount of from 3 to 10% by weight.

3. The composition of claim 1 wherein R is hydrogen.

4. The composition of claim 1 wherein the pH is 6.

5. The composition of claim 1 wherein A is sodium.

6. A cosmetic moisturizing composition consisting essentially of a water and ethanol solution having a pH between 5 and 7 containing from 1% to 20% by weight of at least one polyaldehydopolycarboxyl polymer having a polymer chain containing substantially units selected from the group consisting of

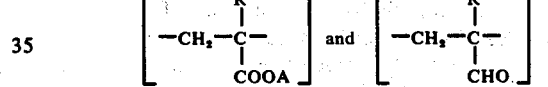

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyaldehydopolycarboxyl polymer having a ratio of —COOA groups to C=O groups of from 0.5:1 to 16:1 and and a degree of polymerization of from 3 to 100; and the remainder inert cosmetic excipients.

7. A process for maintaining a certain hygroscopicity for the protection of the skin of warm-blooded animals comprising topically applying to the skin a safe but effective amount as a moisturizing agent of a cosmetic composition consisting essentially of an emulsion having a pH between 5 and 7 containing an emulsifier, from 1 to 20% by weight of at least one polyaldehydopolycarboxyl polymer having a polymer chain containing substantially units selected from the group consisting of

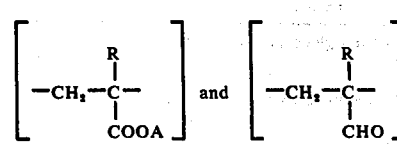

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyaldehydopolycarboxyl polymer having a ratio of —COOA Groups to C=O groups of from 0.5:1 to 16:1 and a degree of polymerization of from 3 to 100, and the remainder inert cosmetic excipients, said emulsion being selected from the group consisting of oil-in-water emulsions and water-in-oil emulsions.

8. The process of claim 7 wherein said polyaldehydopolycarboxyl polymer is present in an amount of from 3 to 10% by weight.

9. The process of claim 7 wherein said ratio of —COOA groups to C=O groups is from 2:1 to 9:1.

10. A process for the maintaining a certain hygroscopicity for the protection of the skin of warm-blooded animals comprising topically applying to the skin a safe but effective amount as a moisturizing agent of a cosmetic composition consisting essentially of a water and ethanol solution having a pH between 5 and 7 containing from 1 to 20% by weight of at least one polyaldehydopolycarboxyl polymer having a polymer chain containing substantially units selected from the group consisting of

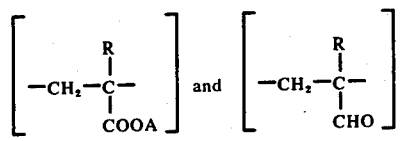

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyaldehydopolycarboxyl polymer having a ratio of —COOA groups to C=O groups of from 0.5:1 to 16:1 and a degree of polymerization of from 3 to 100; and the remainder inert cosmetic excipients.

* * * * *